US005976847A

United States Patent [19]

Hermann

[11] Patent Number: 5,976,847

[45] Date of Patent: Nov. 2, 1999

[54] HYDROPHILIC URETHANE BINDER IMMOBILIZING ORGANISMS HAVING ACTIVE SITES FOR BINDING NOXIOUS MATERIALS

[76] Inventor: Paul Hermann, 21 Fieldstone Dr., Dover, N.H. 03820

[21] Appl. No.: 08/686,611

[22] Filed: Jul. 24, 1996

[51] Int. Cl.[6] .......................... C12N 11/04; C12N 11/02; C12N 11/08; C02F 3/00

[52] U.S. Cl. .......................... 435/182; 435/177; 435/180; 435/262.5

[58] Field of Search .................................... 435/177, 180, 435/182, 262.5

[56] References Cited

U.S. PATENT DOCUMENTS

| | | | |
|---|---|---|---|
| 3,694,301 | 9/1972 | Gruenewald et al. | 161/159 |
| 3,805,532 | 4/1974 | Kistner | 61/36 R |
| 4,137,200 | 1/1979 | Wood et al. | 521/159 |
| 4,329,436 | 5/1982 | Dedolph | 521/99 |
| 4,456,685 | 6/1984 | Guthrie | 435/109 |
| 4,828,542 | 5/1989 | Hermann | 604/3 |
| 4,983,299 | 1/1991 | Lupton et al. | 210/617 |
| 5,011,604 | 4/1991 | Wilde et al. | 210/602 |
| 5,120,441 | 6/1992 | Jackson et al. | 210/602 |
| 5,256,703 | 10/1993 | Hermann et al. | 521/120 |
| 5,405,648 | 4/1995 | Hermann | 427/213.31 |

OTHER PUBLICATIONS

FUSEE, Murray C., Wayne E. SWANN, and Gary J. CALTON. "Immobilization of *Escherichia coli*Cells Containing Aspartase Activity with Polyurethane and Its Application of L–Aspartic Acid Production", Applied and Environmental Microbiology. Oct. 1981: vol. 42, No. 4, pp. 672, 676.

*Primary Examiner*—David M. Naff
*Attorney, Agent, or Firm*—David and Bujold

[57] ABSTRACT

A composite biosorption material is formed of a hydrophilic urethane binder containing immobilized bioactive organisms of at least about one micron in size and having active sites for binding and removing noxious materials such as metal ions from an effluent such as a waste water stream. To form the composite, a prepolymer is prepared by heating polyethylene glycol, having an average molecular weight of about 1000, to over 200° F. up to 350° F., preferably greater than 220° F., and reacting a diisocyanate with the heated polyethylene glycol while mixing to form the prepolymer. After cooling, the prepolymer is mixed with an aqueous slurry containing the organisms such as *Datura innoxia* cells, and optionally a surfactant and bactericide, in a weight ratio such as 1:1 to 6:1, and the resultant mixture is cured to form the composite material containing a dry weight of the organisms such as about 15% to 90%. The diisocyanate may be a mixture of toluene diisocyanate 2-4 and toluene diisocyanate 2-6, and at a ratio of diisocyanate to polyethylene glycol to stoichiometrically end cap the polyethylene glycol with a content of isocyanate groups of between 2% and 14%.

16 Claims, 5 Drawing Sheets

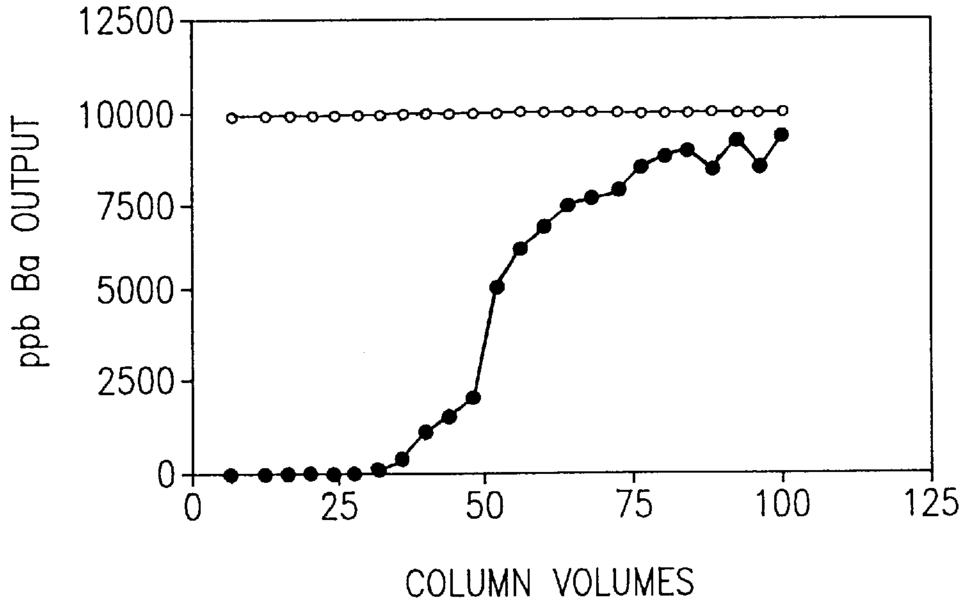

A SOLUTION CONTAINING 10,000 PART/BILLION OF Ba(II) WAS PASSED THROUGH A COLUMN CONTAINING NON-VIABLE DATURA INNOXIA CELLS IMMOBILIZED IN A 30% POLYMER SPONGE. THE Ba CONCENTRATION IN THE FILTRATE WAS THEN MEASURED AND THIS CONCENTRATION IS PLOTTED AGAINST THE NUMBER OF COLUMN VOLUMES OF Ba(II) SOLUTION TREATED. ONE COLUMN VOLUME EQUALS THE VOLUME OF LIQUID THAT WILL OCCUPY THE EMPTY COLUMN MINUS THE VOLUME OCCUPIED BY THE SPONGE:PLANT CELL MATRIX.

ppb Ba INPUT —o— ppb Ba OUTPUT —●—

FIG.5

HYDROPHILIC URETHANE BINDER IMMOBILIZING ORGANISMS HAVING ACTIVE SITES FOR BINDING NOXIOUS MATERIALS

FIELD OF THE INVENTION

This invention relates to immobilizing biological material used in bioremoval concentration to remove noxious materials such as metal ions. Specifically, this invention relates a composite material and method for immobilization of a biomass that will remove noxious materials and metal ions from a waste water stream.

BACKGROUND OF THE INVENTION

Biosorption may be simply defined as the removal of metal or metalloid species, compounds and particles from solution by biological material. This is a general definition which takes no account the mechanistic details and, although virtually all biological material has a significant biosorptive ability, the concept and application of biosorption has mainly been directed towards microbial systems. Micro-organisms, including bacteria, algae, fungi and yeasts, efficiently accumulate organics, heavy metals and radionuclides from the external environment. The amounts taken up are relatively large and a variety of mechanisms may be involved, including adsorption as well as processes dependent on metabolism. Living and dead cells as well as excreted or derived products, e.g. cell wall constituents, pigments and polysaccharides, are also capable of contaminant removal from solution.

Biosorption is currently of industrial interest because the removal of toxic organic compounds, heavy metals and radionuclides from liquid waste streams can result in detoxification and, therefore, safe environmental discharge. Subsequent treatment of loaded biomass can enable recovery of valuable elements, or further containment of highly toxic and/or radioactive species. With accelerated depletion of natural mineral sources, there is a greater need of recycling of metals while ore efficient means of effluent detoxification must be devised for environmental protection.

Biomass-based technologies provide an alternative or supplement to conventional methods of metal removal or recovery including ion exchange resins, recrystallization, reverse osmosis, precipitation and electrodialysis.

The walls of bacteria, algae and fungi are efficient metal biosorbents and in many bases, initial binding may be followed by inorganic deposition of increased amounts of metal, even up to 50 percent of the dry weight. Ionic and covalent bonding may be involved in biosorption, with constituents such as proteins and polysaccharides also playing important roles. In several species, biosorption may be the largest proportion of total uptake. This is especially true for metals such as lead (Pb) and aluminum (Al) and radionuclides like Uranium and Thorium. Variations in the composition of microbial cell walls, which can be influenced by cultural conditions, can result in considerable variation in biosorptive capacity which enable some degree of selective accumulation, although biosorption may be largely determined by the chemical behavior of the metal species involved. Particulate material, as well as dissolved metals, can also bind to biomass, e.g. suphides of copper, zinc and lead, zinc dust and ferric hydroxide.

For industrial applications, using freely suspended microbial biomass has several disadvantages, including small particle size and low mechanical strength, while a similarity of density with the effluent can limit the choice of bioreactor design even to the point of making biomass/effluent separation difficult. Immobilized biomass has a greater potential in a packed-bed or a fluidized-bed reactor with the benefits including control of particle size, better capability of regeneration and re-use of the biomass, ease of separation of effluent from the biomass for recirculation, high biomass loadings and minimal clogging in a continuous flow system. Furthermore, immobilized systems may be mathematically defined by reference to such parameters as flow rate, metal concentration and loading capacity. Immobilized systems particularly lend themselves to non-destructive recovery, and after metal-loading, the metal may be concentrated in a small volume of solid material or desorbed into a small volume of eluant for recovery, disposal or containment.

The method of immobilization has a significant influence on removal efficiency. Simple electrostatic adsorption of cells to surfaces is weak, affected by pH, and prone to washout by the flow of effluent over the media. Chemical coupling engenders toxic symptoms which reduce efficacy of the biomass. Prior art entrapment of cells within alginates, polyacrylamide and silica gels can be highly efficient in small-scale systems, though diffusional limitations are a problem.

There is, therefore, a need for an improvement over the known art to overcome the current disadvantages and to provide an economical solution.

The invention herein solves these problems and is compatible with liquid systems.

The invention specifically outlines the process of combining a bioagent, for example the bioagent, non-viable *Datura innoxia* cells and a polyurethane binder, as taught in U.S. Pat. No. 5,120,441. To those skilled in the art, it will become apparent that substitution of *Datura innoxia* plant cells with other plant species or other biomass (herein collectively referred to as an "active material") may be used in the present invention without detracting from breadth or scope of the invention herein.

Active ingredient biomass materials are well known to those skilled in the art and are further defined in Biochemical Nomenclature, Biochemical Society 1978, Enzyme Nomenclature, 1984 Academic Press, Orlando, Fla.

Use of biomass algae for removal of pollutants from a power plant discharge is disclosed in U.S. Pat. No. 5,011, 604. Active ingredient biomass materials immobilized with the present invention include, but are not limited to the bioagents listed below:

| | |
|---|---|
| *Datura innoxia* | Plant cells |
| Casein Hydrosolate | Enzymes |
| Cyanidium | Algae |
| Green Tea | Plant cells |
| Pseudomonus | Bacteria |

Many binder systems might look appealing, but the hydrophilic characteristics of the present invention allow the effluent stream to come into intimate contact with the immobilized biomass. This is explained by the fact that any blocking of metal-binding sites of the biomass by the hydrophilic binder is offset by the hydrophilic nature of the described binder allowing the effluent to pass readily through the film of hydrophilic binder to come into contact with the surface of the biomass material suspended in the composite material of the present invention active ingredients.

It is well known that a reduction in particle size, while still maintaining the same weight volume, increases the surface area. However, discrete micron sized individual biomass particles rapidly pack in columns when subjected to increased liquid pressure and such packing causes significant pressure drop. Therefore, larger granules of biomass are used in a conventional filtration device to reduce the pressure drop. Utilizing the invention herein, binds together micron sized discrete individual biomass particles, containing the active ingredients, which allows a reduction of biomass size relative to prior art designs, increasing the available surface area and maximizing the available metal-binding or contaminant adsorption sites.

Envision in a particular prior art format, activated carbon is used as an active absorbent, a ⅛" diameter particle whose outside surface is the only area available to react with the effluent. The biomass sites on its outside surface in contact with effluent removes metal and/or noxious materials from the effluent. However, the interior volume of the activated carbon does not contact the effluent and is useless. Compare this to a powder of smaller particle size of the same weight of activated carbon. The available surface area of the smaller particle sample increase up to 1500 times depending on particle size. The surface to volume ratio of the smaller particle is much higher and up to 90–95% of the available binding sites will be available to interact with the effluent.

SUMMARY OF THE INVENTION

The present invention provides a new composite material comprising active biomass particles suspended in a binder support system. The composite may be ground into particular form of desired particle size to allow improved effluent flow over said composite particle beds. The pressure drop is minimized by binding the biomass with a plurality of individual micron size particles made of hydrophilic carrier or binder system, and spacing them apart by the physical sized and shape of the composite. Binding in this format also sets up a matrix containing microporous spaces, between biomass particles, that allows the capillary forces to increase the absorption efficiency. A plurality of the bound discrete individual biomass particles are readily ground into any specific size with a conventional grinding equipment such as a Cumberland grinder. Thus, a bound biomass is then able to be reduced to any required particle size which may then be supported on a filter screen while allowing the effluent to readily flow through the particle bed with minimal pressure drop. The composite of the present invention can be formed into various shapes and forms that lend themselves to various applications. The composite can be formed into sheets, specific shapes, molded parts and/or granulated particles, and the like.

The binder system can include, but is not limited to, urethane polyester epoxy, other. thermoset materials, polyethylene oxide, natural gums, combinations of gums and carboxy methyl cellulose and other hydrogen bonding materials. Also possible are latexes, glues and adhesives that are water soluble in processes, hydrophilic in nature, but insoluble in water after processing.

Two binder systems useful in the practice of the present invention Prepolymer systems commercially available from W. R. Grace & Co. under the trademark "HYPOL" and Twin Rivers Engineering of Boothbay, Me., under the trademark "TREPOL"—see U.S. Pat. Nos. 3,805,532; 4,137,200; 4,456,685 and 4,828,542. These state of the art systems teach a urethane foam product produced from a prepolymer including isocyanate and polyethylene glycols to create hydrophilic properties. Most state of the art systems contain trifunctional glycols, such as trimethylopropane, that detract from hydrophilic properties and deter from the objects of this invention. All prior art materials create a foamed cellular structure, when reacted with water space the active particles further apart than wanted. The preferred embodiment is a polyethylene glycol of 1000 molecular weight glycol, end-capped with TDI, reacted together as a prepolymer under specific temperature conditions. Surprisingly, it has been found that, when blending the preferred prepolymer with an active ingredient slurry (biomass in water), surfactant and/or solvent in precise proportions, the binding can be formed with the desired characteristics.

The required characteristics of the binder process include, but are not limited to: closely adjacent discrete individual biomass particles being bound together with a hydrophilic binder which minimizes washout, minimizes cellular foam, is not cytotoxic to cells, has a low exothermic reaction temperature, a low pH drift during the reaction, and is able to be depdlymerized conveniently after use.

Wherefore, it is an object of the present invention to overcome the problems and drawbacks associated with the state of the art designs.

It is therefore an object of the invention to provide a new composite material to efficiently reduce the volume of hazardous radioactive and/or toxic metal contaminated waste contained in waste effluent and reduce the amount of material to be stored by 10,000 to 1,000,000 fold, depending on initial concentrations.

Another object of the invention is to provide a new composite material capable of substantially reducing the concentration of TNT in aqueous solutions.

There are over 10,000 electroplating facilities in the United States each producing an average of 55,000 gallons of waste on a daily basis. Such waste contains a total of 300 ppm of heavy metals which are considered toxic. Disposal of such waste costs on average $400 for each 55 gallon drum. It is, therefore, an object of this invention to remove the low volume of heavy metals in order to reduce the disposal cost.

Trichloroethylene (TCE), a solvent used commercially for over 50 years, has been found to be carcinogenic and so its use has been limited. It is now a significant pollutant of potable drinking water throughout the United States. It is therefore another object of this invention to degrade TCE in water systems.

It is a further object of this invention to facilitate adsorption of toxic materials, heavy metals, radwaste, and/or degradation of same, or binding of these materials to the composite material of the present invention. In some cases, such as electroplating, heavy metal recovery is desired. In other instances, such as radwaste, incineration might be a further process. In all cases, it is beneficial and also an object of the invention to provide an immobilized composite material which may be depolymerized simply by contact with bleach.

Recovery of metals adsorbed or bound to composite materials is possible through a change in pH or contacting with a salt which is another object of the invention.

The invention will remove almost any noxious material by properly selecting the biomass, immobilizing it, contacting the proper biomass with the noxious material, collecting it, degrading it, separating it and allowing it to be properly disposed of or reused.

Another object of the invention is to a composite material for attraction and removal of noxious material from an effluent stream comprising a plurality of discrete individual biomass particles; and a hydrophilic binder wherein said biomass particles are bound in said hydrophilic binder to form an immobilized bound biomass having spaces formed between adjacent individual biomass particles thereby increasing active surface area.

The present invention relates to a method of forming a composite material for attraction and removal of any noxious material from an effluent, said method comprising the steps of: providing a plurality of discrete individual biomass particles; and bonding the plurality of discrete individual biomass particles together with a hydrophilic binder to form an immobilized bound biomass with an increased active surface area.

The present invention also relates to a method for binding noxious material comprising the steps of: a) selecting a biomass; b) immobilizing the biomass by adding hydrophilic binder; c) introducing the biomass to a noxious material to form a biomass-contaminated product; d) collecting the biomass contaminated product; e) degrading the noxious contained biomass; and f) separating the noxious materials from the biomass.

BRIEF DESCRIPTION OF THE DRAWINGS

The invention will now be described, by way of example, with reference to the accompanying drawings in which:

FIG. 5 is a graph showing removal of Ba from a solution containing 10,000 ppb Pa using non-viable plant cells immobilized in a 30% sponge matrix.

DISCLOSURE OF INVENTION AND PREFERRED EMBODIMENT

Figure 1:
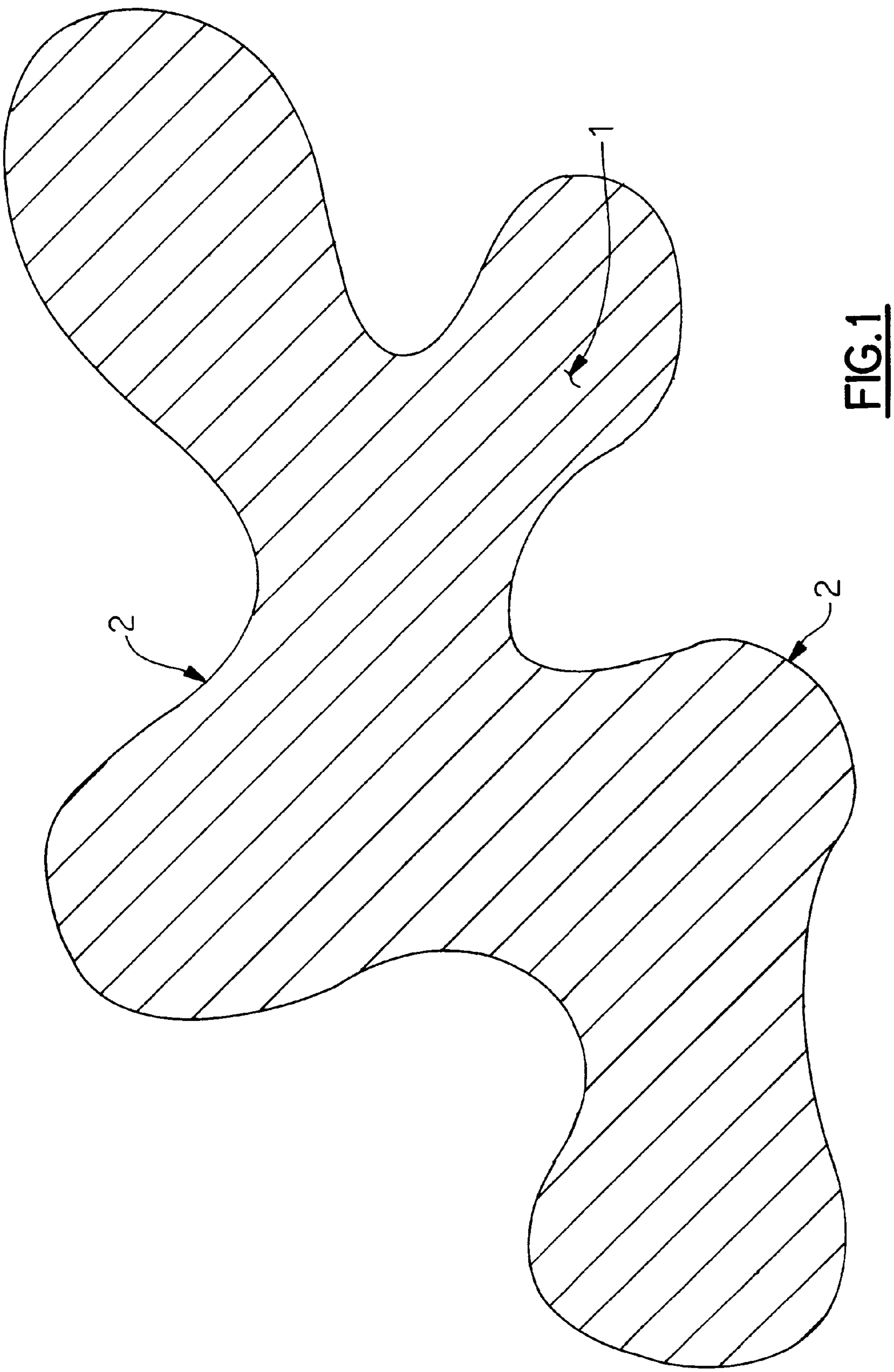
FIG. 1 is detailed cross section of an active ingredient biomass material imbedded in hydrophilic binder.

A description of the preferred embodiment of the present invention, which includes the use of a hydrophilic binder sold by Matrix R & D Corporation of Dover, N.H. under the "BIPOL" trademark, now follows. The preferred hydrophilic binder, sold under the trade-mark "BIPOL", is prepared by reacting a prepolymer substantially linear isocyanate capped polyether polyol derived from difunctional active hydrogen containing initiator, e.g. an aliphatic diol such as ethylene glycol, propylene glycol or 1,4 butanediol and one or more 1,2-epoxides which will impart hydrophilic properties to the resulting polyol, e.g. ethylene oxide or propylene oxide. Polyols of this type are well known and there are numerous commercially available materials. The preferred polyether polyols are derived from ethylene glycol and ethylene oxide and may be represented by the general formula:

$$H(OCH{=}CH\ )m\ OCH{=}CH\ O(CH{=}CH\ O)n\ H$$

wherein m and n each are an integer of from 2 to about 250 and preferably from about 5 to about 80, and m and n taken together is an integer of from about 3 to about 500 and preferably from about 20 to about 200. In terms of their average molecular weights. These polyols can range from about 200 to about 20,000 and preferably from about 800 to about 10,000.

The selected linear polyether polyol is reacted, or capped, with an amount of a diisocyanate calculated to provide a correspondingly substantially linear prepolymer having an average reactive functionality of about 2.0. Suitable diisocyanates include toluene-2, 4-diisocyanate, toluene-2-6 diisocyanate, commercial mixtures of toluene-2-4- and 2,6 diisocyanates, cyclohexylene-1,4-diisocyanate, m-phenylene diisocyanate, 3,3-diphenyl-4,4-biphenylene diisocyanate, 4,4-biphenylene diisocyanate, 1,6-hexamethylene diisocyanate, 1,5-naphthalene diisocyanate, cumene-2,4-diisocyanate, 2,4-diisocyanatodiphenylether, 5,6-dimethyl-1,3-phenylenediisocyanate, 2,4 dimethyl-1-3-phenylene-diisocyanate, 2,4-dimethyl-1,3-phenylenediisocyanate, 4,4-diisocyanatodiphenylether, 9,10-anthracene diisocyanate, 2,4-diisocyanatotoluene, 1,4-anthracene diisocyanate, 2,4,6-toluene triisocyanate, isophorone diisocyanate and p,p',p"-triphenylemethane triisocyanate. Toluene-2,4-diisocyanate and diisocyanate mixtures containing toluene-2-4-diisocyanate are especially preferred due to their relatively low cost and ready commercial availability.

To effect reaction, the prepolymer is reacted with a relatively large molar excess of water. The water can be provided as water per se, preferable deionized water, or as an aqueous solution containing one or more of the components of the composite. When desired, the prepolymer and/or the aqueous components can contain one or more active ingredients. However, since the isocyanate groups of the prepolymer are quite reactive, in most cases the active ingredient will be added to the aqueous component, if necessary, employing a mutual solvent, emulsified or dispersing agent if the active ingredient is insoluble in water.

Immobilization of live biomass is accomplished without destruction by adding the biomass to an aqueous phase in a range of 1–50% by weight of the aqueous phase, added surfactant and optionally a bactericide, mixing the aqueous phase with the prepolymer (which is independently formulated and reacted at a temperature over 200° F. and up tp 350° F.) so as to produce allophonates and chain extension in an otherwise linear prepolymer with NCO values from 2%–14%. The aqueous phase and prepolymer are generally mixed in a ratio by weight of at least approximately 5:1 or greater, preferably 1:1–6:1 maximizing dry solids content of the biomass in a range 15%–90%. Upon polymerization of the composite, the biomass particles are distributed over, intimately bonded to and spaced within the hydrophilic polymer composite yet accessible to effluent.

Very little cellular foam is produced and the exothermic temperature reaction (at a temperature less than 110° F.) can be controlled so that the binding capacity of the active ingredients is not significantly altered. Some live biomass cannot survive temperatures in excess of 110° F. without killing or destroying the active ingredients.

Many attempts have been made to immobilize various biomass components (see (1) immobilization of *E Coli* cells, Fusee et al., *Applied and Environmental Microbiology,* October 1981, pg. 672–676; (2) U.S. Pat. No. 3,694,301; (3) U.S. Pat. No. 4,137,200; (4) U.S. Pat. No. 4,456,685). Ref. no. (1) produces foamed cellular product @16% actives wherein use of W. R. Grace & Co. "HYPOL" above 1.79 isocyanate content reduced the biomass activity up to 28%.

Further testing of the W. R. Grace & Co. polymer exhibits less hydrophilicity than Matrix R & D Corporation's "BIPOL" based on the addition of TMOP in polymerization (see U.S. Pat. No. 4,137,200 Ref. (3)).

Hydrophilic urethanes are well known to those skilled in the art (see Ref. (2) U.S. Pat. No. 3,694,301, and "Polyurethane Chemistry and Technology", Saunders and Frisch Part I, Interscience Publishers, New York, 1962). The hydrophilic binder sold under the "BIPOL" trademark is manufactured with chemistry and molar ratios similar to those defined in Reference (2) i.e. U.S. Pat. No. 3,694,301, with the surprising capability of reacting said chemistry at a temperature of between 93–149° C. This reaction temperature is well outside of conventional urethane processes, creates a much high cross link density without the addition of triols which detract from the hydrophilicity, while still maintaining the strength using a linear prepolymer. Ref. (4) U.S. Pat. No. 4,456,685 relates to immobilization of biomass with a MDI based prepolymer which further reduces hydrophilicity and is impervious to depolymerization by 5% sodium hypochlorite solution, e.g. "Clorox", which is an important part of invention herein.

Figure 2:
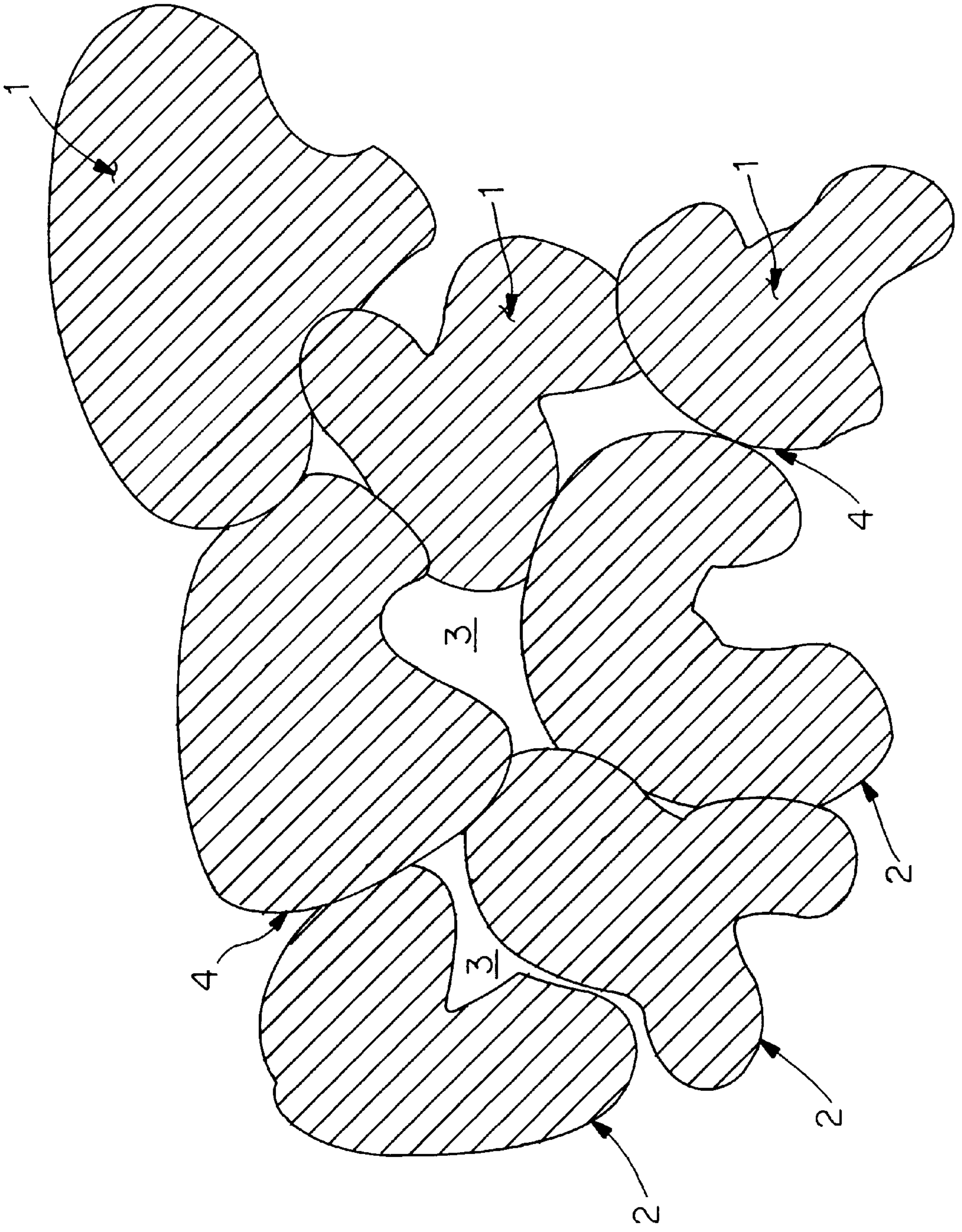
FIG. 2 is a diagrammatic cross section of a plurality of discrete individual biomass particles, as shown in FIG. 1, with air spaces formed between particles.

A diagrammatic drawing of an example of an active ingredient 1, such as *Datura innoxia* suspension of culture cells, reduced to a preferred size and coated with a continuous film of hydrophilic binder 2, is shown in FIG. 1. During polymerization of the aqueous phase containing the active ingredient cells with the urethane pre-polymer, a gas, e.g. $CO_2$, is produced that would normally form a cellular polymerized mass. As shown in FIG. 2, the resultant hydrophilic binder 2 does not contain a cellular structure. It has been found that, by controlling the viscosity of the mixture of the aqueous phase and the pre-polymer, the formed gas bubbles will break prior to polymerization and coat the active ingredient 1 with a layer of hydrophilic binder 2 separated by air spaces 3. It will be appreciated, by those skilled in the art, that the substitution of other biochemical agents or solids, for example lower species such as fungi protista or monera, will coat these materials in a similar fashion.

Figure 3:
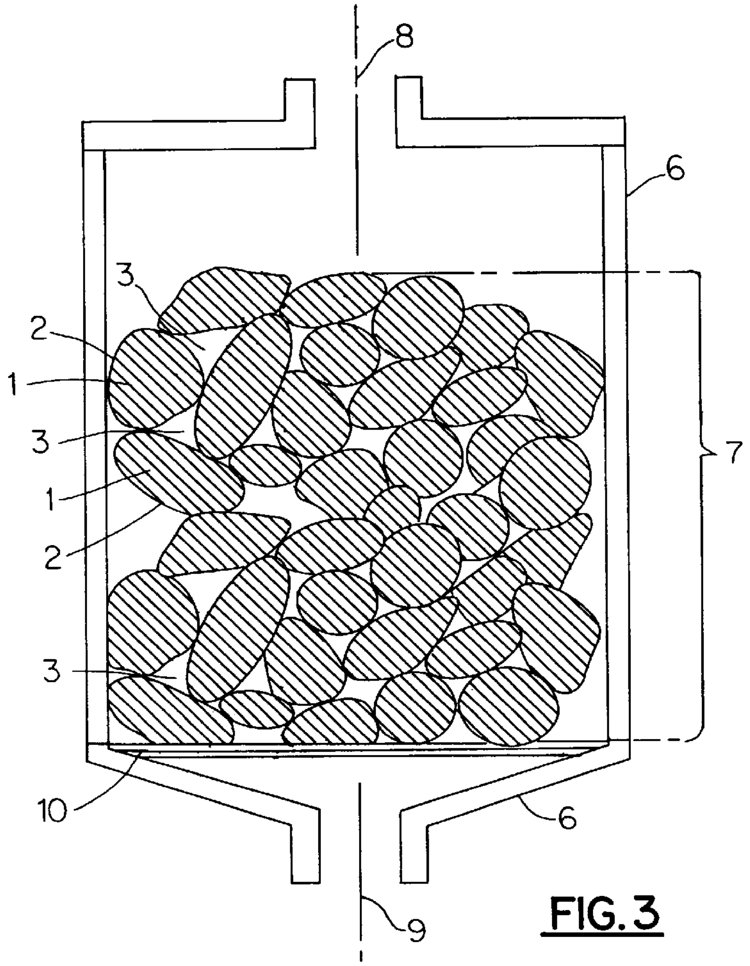
FIG. 3 is a diagrammatic cross section of a filter housing, supplied with an inlet and outlet for an effluent stream flow, in which a plurality of composite particles are supported on a screen.

FIG. 3 shows a filter cartridge 6 with a plurality of granulated particles 7 formed according to FIG. 2. The cartridge is supplied with an inlet 8 and an outlet 9 that is used to pass effluent through said filter and allows contact between noxious components of the aqueous stream and the granulated particles 7. The cartridge also contains a support screen 10 whose hole size will support the granulated particles 7 yet allow flow of effluent therethrough. Sizing of granulated particles 7 will control the pressure drop through the filter.

Figure 4:
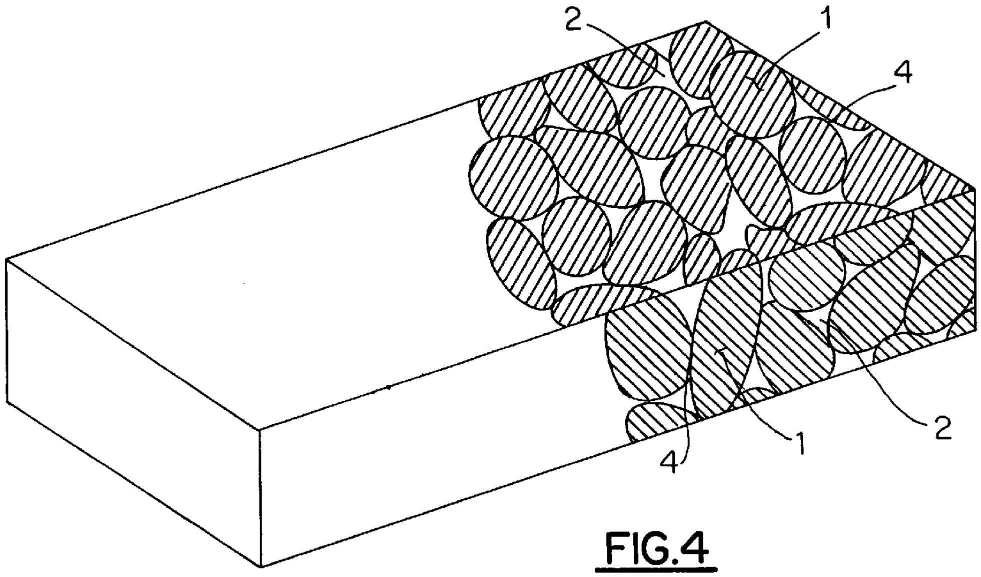
FIG. 4 is a diagrammatic isometric view of a solid sheet die cut or molded of a plurality of particles as shown in FIG. 2.

FIG. 4 shows a rectangular block made up of a plurality of discrete individual active ingredient biomass particles 1 bonded together with hydrophilic binder 2 at contact points 4, wherein the resultant product has not yet been ground into particles of a desired size but has been formed to a desired sheet and cut into a size or shape. It is to be appreciated that the composite material of the present invention can be molded into a three-dimensional shape to satisfy applications where contact of active ingredient cells with noxious materials is better suited in a solid form rather than the granulate particle form shown in FIGS. 1 and 2.

FIG. 5 shows $Ba^{++}$ removal from a solution containing 10,000 ppb $Ba^{++}$. A contaminated solution is passed through a column packed with non-viable *Datura innoxia* cells immobilized in a 30% polymer composite produced in accordance with the teaching of this application.

Figure 6:
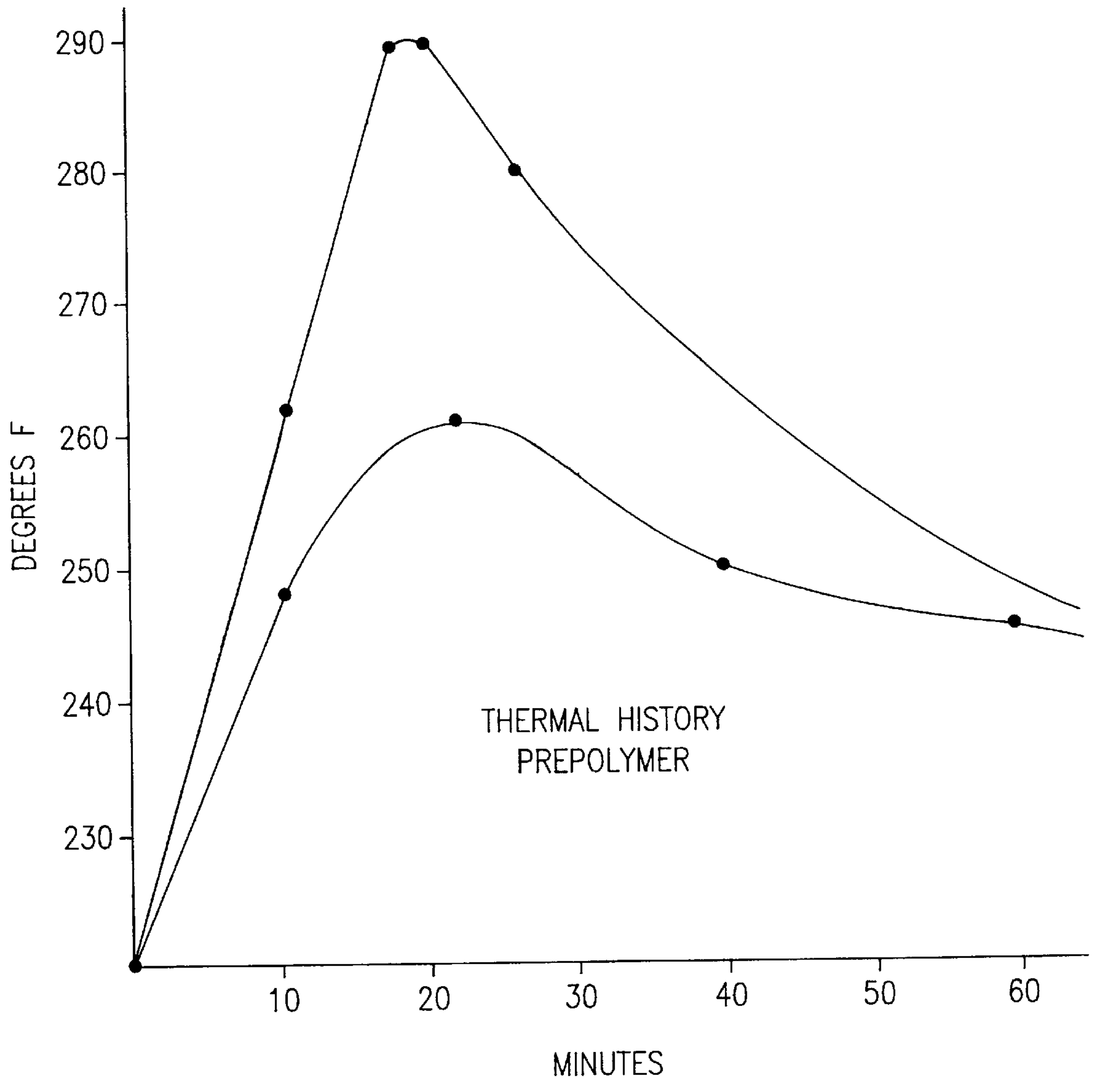
FIG. 6 is a graph showing the "BIPOL" polymer thermal history in its manufacturing reaction.

FIG. 6 shows the acceptable thermal history of the prepolymer reaction during its manufacture.

Preparation of Urethane Prepolymer

Matrix R & D Corporation's urethane prepolymer is prepared by the following process developed well outside the boundaries of known prior art urethane. The diversion of this invention from prior art is twofold. The first differentiation is the order of addition, where isocyanate is added to the polyol instead of vice versa, and the second is where the reaction temperature is initiated above 220° F. It has been demonstrated that the resultant polymerized urethane prepolymer is more hydrophilic and has a higher tensile strength. The increased tensile strength is believed to be created by more allophonate production. The prepolymer is lower in viscosity than the prior art which has similar NCO.

The following example typifies the deviation from prior art and would not be considered possible by those skilled in urethane reaction processes because of concern relating to gelation.

Materials:

Union Carbide "Carbowax 1000";

1000 molecular wt. polyethylene glycol (PEG); and

Bayer 2,4-2-6 TDI.

A 250 gallon jacketed tank was charged with 500 lbs. of PEG and, stirring under anhydrous conditions, was brought up to a temperature of 220° F. 175.5 lbs. of TDI, at room temperature, was pumped into the PEG at a rate of approximately 18.9 pounds/minute and the exothermic reaction peaked at a temperature of about 290° F. within 20 minutes.

When the reaction of the prepolymer was completed, the temperature dropped to 250° F. within 1½ hours at which time prepolymer was decanted into drums.

Variations on the stoichiometry of chemicals allow NCO values between 5–13 by conventional formulations. Viscosities have ranged 5000 CPS-12000 CPS @90° F, all functional.

A thermal history curve was prepared for varying conditions (see FIG. 6) with materials falling within the boundaries found acceptable.

Excursions into the thermal histories submitted within start at the upper limit of 200° F. for conventional urethane reactions of prior art. Standard testing of polymerized end product differentials such as tensile strength, hydrophilicity and TDA analysis have proven application acceptance in results.

Preparation of *Datura innoxia* Cells (Example Process)

*Datura innoxia* cells are produced by the following protocol and process (see U.S. Pat. No. 5,120,441).

Cells are grown in baffled Delong flasks (250 ml to 2 liters) at ⅕ the flask volume (i.e. 100 ml cell suspension in 500 ml flask). Cells are aerated by shaking on a platform rotary shaker (120 rpm). Cell growth occurs at a temperature of between 20 and 33° C. However, maximum growth rate (doubling in biomass every 22–24 hours) is between a temperature of 30–33° C. Cultures are not viable above 34° C. Below 20° C. cell growth is very slow. Cell cultures grow well with a pH range from 5.0 to 6.2.

The combination of MATRIX's "BIPOL" 2 and *Datura innoxia* cells 1 spatially separated by air space 3 yet bound together are diagrammatically represented by FIG. 2.

EXAMPLE 1

*Datura innoxia* cells, grown as above, were dried to produce a fine powder. For the purposes of the following examples, a particle size distribution between 4–65 mesh size was chosen. The dry powder was used to facilitate proper ratio of water to powder, as well as to facilitate the shipment of the powder without the possibility of any microbial growth in the cell slurry.

An aqueous phase was prepared by combining:

62 ml water; and 8 grams cell powder.

The resultant aqueous phase was a pumpable slurry that would not settle out of suspension and contained a large number of *Datura innoxia* cells. A small volume of F88 (BASF) surfactant and GERMABEN II (SUTTON) bactericide approximately 0.5% weight of each was added to the water phase to decrease the surface tension and eliminate bacterial and other germicidal activity.

Thirty grams of the "BIPOL" prepolymer was well blended with the above proposed aqueous phase.

The resultant well mixed slurry was then formed into a sheet and/or a bun stock and allowed to cure. The dry composite material consisted of approximately 21% (w/v) cells.

EXAMPLE 2

To increase the percentage of cells per unit of dry composite material, an aqueous phase was prepared as follows:

| | |
|---|---|
| surfactant bactericide water | 74.0%; |
| *Datura innoxia* cells | 23.2; |
| coupling agent | 0.5; and |
| dispersant | 2.3. |

As with Example 1, the "BIPOL" was well blended with the aqueous phase at a ratio of aqueous phase to polymer of 4.32:1.

EXAMPLE 3

A surprisingly non-conventional method of preparing the novel composite material, according to the present invention, is to combine the components in the following order.

The unique process of the present invention eliminates the need for costly urethane foam metering and mixing equipment and allows the manufacture of the novel composite material on site. Even for large quantities of material, a scale necessary to weigh components and a low-cost cement mixer are the only required equipment.

EXAMPLES 3, 4 and 5

Examples 3, 4 and 5 show the variety and flexibility of the formulation and the percentage of cells in the final product. The loading of cell was also changed: the "BIPOL" was reduced by 50% dilution with an ester based solvent "DBE" (Dibasic Ester)(DUPONT). The listed ingredients were added in the following order to a conventional cement mixer.

| | EX 3 | EX 4 | EX 5 |
|---|---|---|---|
| CELLS | 11.5 lbs. | 30.12 lbs. | 38.75 lbs |
| SURFACTANT WATER BACTERICIDE | 82.17 | 56.32 | 50.38 |
| BIPOL | 6.3 | | |
| 50% SOL BIPOL AND DBE | | 13.5 | 10.85 |
| % ACTIVE CELLS/ DRY FOAM | 64.0% | 81.6% | 87.0% |

To determine the increase in particle size distribution while immobilizing the cells in Examples 4 and 5, a control sample of untreated cells was sieved and analyzed in comparison to Examples 4 and 5. The following results were obtained:

| | | % PARTICLES | |
|---|---|---|---|
| SCREEN SIZE | CONTROL | EX. 4 | EX. 5 |
| 4 | 1.0 | 9.3 | 13.5 |
| 18 | 35.7 | 72.1 | 60.3 |
| 20 | 2.1 | 7.7 | 7.2 |
| 40 | 10.5 | 10.6 | 18.9 |
| 50 | 7.4 | | |
| 70 | 0.2 | | |
| RECEIVER | 23.1 | | |

From the above, it was determined that the particulate size of the control on screen 4 and 18 represents 36.7% of the total. Examples 4 and 5 show 73.8% and 81.4%. This shows the increased particle size distribution capabilities of this invention.

EXAMPLE 6

A composite material made as in Example 2 was granulated by a Cumberland grinder into discrete particles to produce size range of sieve #4-50.

A 100 ml volume of said active ingredient particles was added to a beaker and covered with 130 grams of bleach solution sold commercially as "Clorox". After 15 minutes, the "Clorox" broke down the mass to less than 50 ml or a reduction of more than 50% by volume. On a weight basis, 100 ml of active ingredient volume weighed 12.6 grams. The reduced fraction broken down by "Clorox" weighed 6.7 grams or a 46% reduction by weight. This weight loss correlates to the original 50.8% weight of active ingredient loading in Example 2 and shows a 90% breakdown of urethane component.

The reactant of the breakdown process are believed to be aldehydes and carboxylic acids.

EXAMPLE 7

Another biomass active ingredient, described as a bacteria and identified as Pseudomonus Burkholderia cepacea strain G4 and its constitutive mutant PR 131 available from Gulf Breeze Lab of Florida, was evaluated and tested for the degradation of trichloroethylene in waste streams as follows.

Thirteen formulations were evaluated to determine the optimal combination of PR 131, the surfactant, the temperature of reaction, the mixing shear, and the residual TDA in the binder.

It was determined by passing water through resultant granulated particles that washout or lack of binding was effected by the type and the amount of surfactant with a 0.016% level of lecithin based surfactant proving optimal. Increasing the biomass density from $3.7\times10^{10}$ to $8.5\times10^{10}$ cells per gram of product also caused fewer cells to be lost.

Cell viability tested by consumed $O_2$ and evolved $CO_2$ showed no difference between immobilized PR 131 or unembedded control, reducing reaction temperature from 70–40° F. nor reduction of TDA levels or shear effect it.

Testing of TCE removal was accomplished by contact of bound particles vs. non-embedded control. TCE degradation was similar.

The preferred embodiment was then defined as:

| | TOTAL FORMULA | DRY SOLIDS | % DRY SOLIDS |
|---|---|---|---|
| PR 131 15% Solids Sol | 59.05% | 8.85 | 18.35 |
| Amisol HS-3 Surfactant 1% Sol | 1.59 | .0159 | .032 |
| BIPOL | 39.36 | 39.36 | 81.61 |

Test results of Example 7

Washout of Embedded Cells

<2%

Viability of Cells

Viable not culturable

Degradation of TCE

Similar to unembedded cells

EXAMPLE 8

A similar set of formulations, as in Example 7, was prepared substituting algae for the bacteria and this showed metal removal.

EXAMPLE 9

A set of formulations was the prepared utilizing Green tea as follows:

| | |
|---|---|
| Water | 50%; |
| F88 Surfactant 1% | 39.6%; |
| Green Tea | 10.3%; |
| Guar Gum | 0.116%; and |
| BIPOL | 33.33%. |

The above formula was formed as sheet and also impregnated onto a non-woven fiber. Testing of resultant non-woven fiber composite showed significant results in absorbing cigarette smoke in an air filtration system.

EXAMPLE 10

The water fern Azolla is known for its removal of heavy metal ions from water (see U.S. Pat. No. 5,000,852). A formulation was prepared utilizing Azolla as follows:

| | |
|---|---|
| F88 Surfactant 1% sol | 59.49%; |
| Azolla | 15.47%; |
| Guar Gum | 0.15%; and |
| BIPOL | 25.08%. |

The present technology produced active metal-binding cells bound together with a binder system that is hydrophilic. The hydrophilic nature of the system brings the effluent stream into close contact with the active ingredient metal binding sites of the cells.

Individual tests show that the active ingredients, immobilized with the above binder, can be more than twice as effective as cells immobilized by other conventional means using various hydrophobic adhesives and polymers.

While the invention has been described by reference to particular embodiments, it is intended to cover all variations and equivalents within the scope of the following claims. In addition, since certain changes may be made in the above described material and process, without departing from the spirit and scope of the invention herein involved, it is intended that all of the subject matter of the above description or shown in the accompanying drawings shall be interpreted merely as examples illustrating the inventive concept herein and shall not be construed as limiting the invention.

KINGDOM OUTLINE ORGANISMS

1. MONERA
   Prokaryotic
   Includes; bacteria blue-green algae mycoplasms
2. PROTISTA
   Eukaryotic
   Includes; protozoa some algae slime mold
3. FUNGI
   Includes; true fungi
4. PLANTAE
   Most algae all green plants
   Includes; brown algae red algae green algae mosses and liverworts vascular plants
5. ANIMALIA
   Multicellular animals

I claim:

1. A composite material comprising a hydrophilic urethane binder containing immobilized therein a plurality of bioactive organisms at least about one micron in size having active sites on their outside surfaces capable of binding noxious materials evenly distributed in said urethane binder such that said urethane binder does not prevent the sites from binding noxious materials, said composite material prepared by the following steps:

heating polyethylene glycol, having an average molecular weight of about 1000, to a temperature greater than 220° F., adding a diisocyanate to the heated polyethylene glycol while throughly mixing said polyethylene glycol during said adding to react said diisocyanate with said polyethylene glycol at said temperature while mixing to form a prepolymer;

suspending a plurality of bioactive organisms, being at least about one micron in size and having active sites on their outside surfaces capable of binding noxious materials, in an aqueous solution to form an aqueous slurry;

thoroughly mixing said prepolymer with said aqueous slurry to form a substantially uniform mixture of said prepolymer and said aqueous slurry, said prepolymer being cooled prior to mixing with said slurry to a temperature that does not substantially inactivate said bioactive organisms; and curing said mixture to form said composite material comprising a hydrophilic urethane binder containing a plurality of bioactive organisms immobilized therein, said binder being sufficiently hydrophilic to facilitate intimate contact between said bioactive organisms and an effluent stream containing noxious materials, when said composite material is exposed thereto.

2. The composite material as set forth in claim 1, wherein said bioactive organisms are from an order selected from the group consisting of monera, protista, fungi, plantae and animalia; and the composite material is in the form of a plurality of granulated particles.

3. The composite material as set forth in claim 1, wherein said bioactive organisms are in the range of 1 to 10,000 microns in size.

4. The composite material as set forth in claim 1, wherein said diisocyanate comprises a mixture of toluene diisocyanate 2-4 and toluene diisocyanate 2-6, and the mixture is added to said polyethylene glycol in a ratio to stoichiometrically end cap said polyethylene glycol with reactive isocyanate sites (NCO) which have a content of between 2 and 14%.

5. The composite material as set forth in claim 4, wherein said temperature is greater than 220° F. up to350° F., and said prepolymer is cooled to room temperature prior to mixing with said bioactive organisms.

6. The composite material as set forth in claim 1, wherein said composite material is in the form of a sheet, a molded shape or granulated particles.

7. The composite material as set forth in claim 6, wherein said bioactive organisms comprises between 1% and 90% by weight of said composite material.

8. The composite material as set forth in claim 1, wherein said prepolymer and an antifoaming diluent are combined to form a solution which is mixed with said aqueous slurry of bioactive organisms.

9. A composite material comprising a hydrophilic urethane binder containing immobilized therein a plurality of bioactive organisms at least about one micron in size having active sites on their outside surfaces capable of binding noxious materials evenly distributed in said urethane binder such that said urethane binder does not prevent the sites from binding noxious materials, said composite material prepared by the following steps:

heating polyethylene glycol, having an average molecular weight of about 1000, to a temperature over 220° F. and up to 350° F., adding a diisocyanate to the heated polyethylene glycol while throughly mixing said polyethylene glycol during said adding to react said diisocyanate with said polyethylene glycol at said temperature while mixing for a reaction time of about 20 minutes to form a prepolymer;

suspending a plurality of bioactive organisms, being at least about one micron in size and having active sites on their outside surfaces capable of binding noxious materials, in an aqueous solution to form an aqueous slurry;

thoroughly mixing said prepolymer with said aqueous slurry to form a substantially uniform mixture of said prepolymer and said aqueous slurry, said prepolymer being cooled prior to mixing with said slurry to a temperature that does not substantially inactivate said bioactive organisms; and curing said mixture to form said composite material comprising a hydrophilic urethane binder containing a plurality of bioactive organisms immobilized therein, said binder being sufficiently hydrophilic to facilitate intimate contact between said bioactive organisms and an effluent stream containing noxious materials, when said composite material is exposed thereto.

10. The method as set forth in claim 9, wherein said bioactive organisms are form an order selected from the group consisting of monera, protista, fungi, plantae and animalia.

11. The method as set forth in claim 9, wherein said bioactive organisms range in size from 1 to 10,000 microns.

12. The method as set forth in claim 11, wherein said diisocyanate comprises a mixture of toluene diisocyanate 2-4 and toluene diisocyanate 2-6, and the mixture is added to said polyethylene glycol in a ratio to stoichiometrically end cap said polyethylene glycol with reactive isocyanate sites (NCO) which have a content of between 2% and 14%.

13. The method as set forth in claim 9, wherein said composite material is formed as a sheet, a molded shape or granulated particles.

14. The method as set forth in claim 13, wherein said bioactive organisms comprises between 1% and 90% by weight of said composite material.

15. The method as set forth in claim 9, wherein said prepolymer and an antifoaming diluent are combined to form a solution which is mixed with said slurry of bioactive organisms.

16. A method of removing noxious materials from an effluent stream, the method comprising:

heating polyethylene glycol, having an average molecular weight of about 1000, to a temperature over 220° F. and up to 350° F., adding a diisocyanate to the heated polyethylene glycol while throughly mixing said polyethylene glycol during said adding to react said diisocyanate with said polyethylene glycol at said temperature while mixing to form a prepolymer;

suspending a plurality of bioactive organisms, ranging in size from 1 to 10,000 microns and having active sites on their outside surfaces capable of binding noxious materials, in an aqueous solution to form an aqueous slurry;

thoroughly mixing said prepolymer with said aqueous slurry in a ratio by weight of 1:1 to 6:1 to form a substantially uniform mixture of said prepolymer and said aqueous slurry, said prepolymer being cooled prior to mixing with said slurry to a temperature that does not substantially inactivate said bioactive organisms; and curing said mixture to form a composite material comprising a hydrophilic urethane binder containing said plurality of bioactive organisms immobilized therein, said bioactive organisms being about 15% to 90% by dry weight of said composite material, said urethane binder not preventing the active sites of the bioactive organisms from binding noxious materials, and said binder being sufficiently hydrophilic to facilitate intimate contact between said bioactive organisms and an effluent stream containing noxious materials;

contacting an effluent stream containing noxious material with said composite material whereby said noxious material is removed from said effluent stream by said noxious material binding to said active sites of said bioactive organisms to form a contaminated composite material containing said noxious material; and collecting said contaminated composite material and degrading the collected composite material to dispose of said contaminated composite material.

* * * * *